(12) United States Patent
Arminjon et al.

(10) Patent No.: US 6,333,036 B1
(45) Date of Patent: Dec. 25, 2001

(54) VACCINE COMPOSITION CONTAINING POLYRIBOSYLRIBITOL PHOSPHATE AND METHOD FOR MAKING SAME

(75) Inventors: Francois Arminjon; Jean-René Cartier, both of Lyons (FR)

(73) Assignee: Pasteur Merieux Serums, et Vaccins S.A., Lyons (FR)

( * ) Notice: Subject to any disclaimer, the term of this patent is extended or adjusted under 35 U.S.C. 154(b) by 0 days.

(21) Appl. No.: 08/952,602

(22) PCT Filed: May 24, 1996

(86) PCT No.: PCT/FR96/00791

§ 371 Date: Dec. 30, 1997

§ 102(e) Date: Dec. 30, 1997

(87) PCT Pub. No.: WO96/37222

PCT Pub. Date: Nov. 28, 1996

(30) Foreign Application Priority Data

May 24, 1995  (FR) .................................................. 95 06417

(51) Int. Cl.[7] ....................... A61K 39/102; A61K 39/295
(52) U.S. Cl. ..................... 424/201.1; 424/184.1; 424/197.11; 424/256.1; 424/278.1; 424/831
(58) Field of Search ............................ 424/1.11, 184.11, 424/201.1, 256.1, 278.1, 197.11, 831; 530/810

(56) References Cited

U.S. PATENT DOCUMENTS 5,679,352 * 10/1997 Chong et al. .

FOREIGN PATENT DOCUMENTS

| 0 101 562 | 2/1984 | (EP) . |
| 0 208 375 | 1/1987 | (EP) . |
| 0 320 942 | 6/1989 | (EP) . |
| 93 24148 | 12/1993 | (WO) . |

OTHER PUBLICATIONS

Tizard, An Intro. to Veterinary Immunology, 2nd edition, 1982, p. 35.*
Schneerson et al., Quantitative and Qualitative Analyses of Serum Antibodies Elicited in Adults by *Haemophilus influenzae* Type b and Pneumococcus Type 6A Capsular Polysaccharaide–Tetanus Toxoid Conjugates. Infection and Immunity 52(2):519–528, 1986.*

* cited by examiner

Primary Examiner—Donna C. Wortman
(74) Attorney, Agent, or Firm—Burns, Doane, Swecker & Mathis, L.L.P.

(57) ABSTRACT

Vaccine compositions are disclosed which comprise at least one antigen formed by the capsular polysaccharide of Haemophilus influenzae type b or high molecular weight polyribosylribitol phosphate coupled to tetanus anatoxin.

11 Claims, No Drawings

VACCINE COMPOSITION CONTAINING POLYRIBOSYLRIBITOL PHOSPHATE AND METHOD FOR MAKING SAME

BACKGROUND OF THE INVENTION

1. Field of the Invention

The invention relates to the field of vaccine compositions and more particularly to vaccine compositions comprising at least one antigen formed by the capsular polysaccharide of Haemophilus influenzae type b or high molecular weight polyribosylribitol phosphate coupled to tetanus anatoxin.

2. Description of the Related Art

An antigen which can be used for vaccine purposes in man in order to protect him from infections caused by Haemophilus influenzae type b is known in the prior art, and especially through the article "Quantitative and Qualitative Analyses of Serum Antibodies Elicited in Adults by Haemophilus influenzae Type b and Pneumococcus Type 6A Capsular Polysaccharide Tetanus Toxoid Conjugates" Rachel Schneerson et al, Infect. Immun. May 1986. This antigen is formed by a capsular polysaccharide of the bacteria, polyribosylribitol phosphate (or PRP), which is made T-dependent owing to coupling to a carrier protein, tetanus anatoxin. Trials carried out on rhesus children have shown, as this article reports, that the immune response was at one and the same time greater and earlier if the antigen was associated with aluminium hydroxide. However, as another article entitled "Clinical and Immunologic responses to the capsular polysaccharide of Haemophilus influenzae type b alone or conjugated to tetanus toxoid in 18–23 month-old children", Bo A. Claesson and al, The Journal of Pediatrics, May 1988, points out, it was noticed that this antigen, adsorbed on aluminium hydroxide, was less immunogenic after storage than the antigen kept in saline solution, which may be due to degradation of the polysaccharide.

In order to resolve this problem of stability of the PRP-T, it was proposed in the prior art to lyophilize it. This solution, even though it allows the antigen to retain its immunogenic character in the course of time, shows some disadvantages, however, especially at the manufacturing level; the lyophilization and the particular operations of conditioning which it requires complicates the production process, which increases the cost. In addition, at the time of administration, it is necessary to take up the lyophilizate again, which means that it is necessary to have in addition to the lyophilizate a liquid for taking up this lyophilizate; this operation represents a supplementary constraint for the practitioner and presents, like any manipulation, the risk of being carried out badly.

In addition, a certain number of liquid vaccine combinations possess antigens adsorbed on an aluminium-based adjuvant and it would be advantageous to be able, without loss of immunogenicity, to add the antigen formed by the PRP-T to them. In fact, the solution proposed in the prior art and consisting in a special syringe with two compartments (a first compartment containing the PRP-T in lyophilized form and a second compartment containing the other antigens in aqueous suspension) whose contents are mixed for use only at the time of administration is not satisfactory either at the level of the costs of production or at the level of the operations to be carried out by the practitioner.

It is thus desirable to be able to have a liquid vaccine composition comprising the antigen formed by the PRP-T having a very good immunogenic character retained in the course of time, and whose conditions of manufacture allow production at the lowest cost.

SUMMARY OF THE INVENTION

This invention relates to vaccine compositions capsular polysaccharide of Haemophilus influenzae type b or high molecular weight polyribosylribitol phosphate (PRP) coupled to tetanus anatoxin, as well as an aluminium-based adjuvant. Such a combination permits a stable, liquid vaccine composition wherein each antigen retains its immunogenicity.

BRIEF DESCRIPTION OF THE INVENTION

The invention relates to a vaccine composition comprising at least one antigen formed by the capsular polysaccharide of Haemophilus influenzae type b or high molecular weight polyribosylribitol phosphate coupled to tetanus anatoxin as well as an aluminium-based adjuvant, characterized in that the aluminium-based adjuvant has a point of zero charge of less than approximately 7.2.

It has thus been noticed that, surprisingly, under these conditions, PRP-T retains in the course of time in liquid medium its very good immunogenic character.

According to a particular characteristic of the invention the aluminium-based adjuvant comprises aluminium hydroxides to which anions have been added.

Thus, it is possible to use an adjuvant perfectly qualified for vaccine use while retaining in the PRP-T in liquid medium a very good immunogenicity.

According to another characteristic of the invention, the anions are chosen from amongst the phosphates or the citrates.

Thus, the composition obtained has all the safety guarantees necessary for a vaccine administration.

According to a particular mode of carrying out the invention, the vaccine composition additionally comprises one or more of the vaccine valencies chosen from amongst: diphtheria, tetanus, whooping cough, hepatitis B and poliomyelitis.

It is thus possible to have liquid, stable vaccine combinations in which each antigen retains its immunogenicity, which allows the practitioner, without supplementary manipulation on his part, to vaccinate simultaneously against several illnesses; this allows the costs to be reduced at one and the same time as far as the products are concerned and as far as the number of visits to be made are concerned.

The invention likewise relates to a method of manufacture of a vaccine composition comprising at least one antigen formed by the capsular polysaccharide of Haemophilus influenzae type b or high molecular weight polyribosylribitol phosphate coupled to tetanus anatoxin, characterized in that it consists in adding an adjuvant to the vaccine composition by means of a suspension of aluminium complexes having a point of zero charge of less than approximately 7.2.

The present invention will be better understood by reading the detailed description which will follow.

The antigen formed by the capsular polysaccharide Haemophilus influenzae type b is a linear polymer consisting of ribose, ribitol and phosphoric acid which has the following monomeric structure:

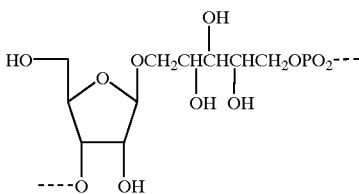

The number of monomers of this type is high (greater than 100), which leads to a polysaccharide whose molecular weight is of the order of 500,000 to 1,000,000.

In order to induce an immune response of the T cells in young children, this antigen is conjugated to a carrier protein formed by tetanus anatoxin.

Such an antigen can, for example, be obtained according to the method described in "Quantitative and Qualitative analysis of serum antibodies elicited in adults by Haemophilus influenzae type b and Pneumococcus type 6A capsular polysaccharide-tetanus toxoid conjugates" Schneerson et al, Infect. Immun. 52: 519 (1986).

The characteristics appropriate to this antigen: high number of monomers of the polysaccharide, nature of the carrier protein, nature of the link between the polysaccharide and the carrier protein, confers particular qualities on it and especially a very good immunogenicity.

In order to retain these qualities in liquid medium in the course of time, it has now been found that it is possible to use aluminium complexes whose point of zero charge is less than approximately 7.2. In fact, it was found that, surprisingly, when the PRP-T is associated with such aluminium complexes, its very good immunogenicity character is retained in the course of time in liquid medium and this takes place whatever its degree of immobilization on the aluminium complexes.

The point of zero charge of aluminium complexes is the equivalent of the isoelectric point of proteins; it is the pH at which the charge at the surface of the aluminium complexes is zero. In fact, this point of zero charge is approached by measurements of zeta potential which can be carried out according to different techniques, the basic method being electrophoresis. It is possible to carry out the measurements by means of an apparatus such as the DELSA 440 of Coulter Electronics, Hialeah, Fla., USA.

The measurement methods and apparatus can be different and the results obtained can likewise vary. The aluminium complexes suitable for the purposes of the invention are those for which this point of zero charge is less than approximately 7.2, this value of 7.2 being only an approximate value.

The aluminium complexes suitable for the purposes of the invention are those which, by nature, have a point of zero charge of less than 7.2 or those which can be modified in order to lower their point of zero charge.

Among the aluminium complexes having by nature a point of zero charge of less than 7.2, it is possible to cite those commonly called aluminium phosphates in the field of vaccine adjuvants, even if, from a chemical point of view, they have salts other than the aluminium phosphates. They are, for example, ADJUFOS® aluminium phosphate supplied by SUPERFOS BIOSECTOR a/s.

They can likewise be aluminium complexes obtained by reaction of sodium carbonate in PBS buffer on potassium and aluminium sulphates.

With such complexes, whether the PRP-T is completely or partially bound to the aluminium complexes, its immunogenicity is retained in the course of time.

Alternatively, it is possible according to the invention to use aluminium complexes which, by nature, have a point of zero charge of greater than 7.2 and which are modified to lower this point of charge.

They are especially aluminium complexes known in the field of vaccine adjuvants as being aluminium hydroxides, even if from a chemical point of view they are not formed exclusively from aluminium hydroxide. They can especially be ALHYDROGEL® aluminium hydroxide supplied by SUPERFOS BIOSECTOR a/s, the product used as an adjuvant in the D.T. Coq™ marketed by PASTEUR MERIEUX S & V or even the product used as an adjuvant in the Recombivax® marketed by MERCK.

According to the invention, the modification of these aluminium complexes consists in the addition of anions. The anions added can be of different nature, on condition that they all have the guarantees of safety necessary for use for vaccine purposes. It has been observed that the addition of citrate ions or phosphate ions would be particularly well suited to the purposes of the invention. The phosphate ions can especially be contributed by a solution containing monopotassium phosphate, disodium phosphate and sodium chloride.

It is likewise possible to use a combination of different anions, for example a combination of phosphate ions and carbonate ions.

It is possible for the anions to be added to the suspension of aluminium complexes prior to the addition of the PRP-T, or for the anions to be added to the PRP-T prior to its contacting with the aluminium complexes. For convenience, it is preferred to suspend the PRP-T in a solution containing the chosen anions before contacting them with the adjuvant.

The quantity of anions added is calculated to lower the point of zero charge of the aluminium complexes used to a value of less than approximately 7.2. This quantity thus varies as a function of the nature of the aluminium complexes used as well as of the quantity of anions possibly contributed by the buffer substances used. Its determination is within the scope of the person skilled in the art.

A vaccine composition stable in the liquid state is thus obtained, that is to say in which the PRP-T retains its good immunogenic character.

It has additionally been observed that, owing to the addition of anions, the immobilization of the PRP-T on the aluminium complexes was reduced, which may contribute to the maintenance of its integrity and thus of its immunogenicity.

Although this is not preferential in the sense of the invention, it is likewise possible to add anions to the aluminium complexes having, by nature, a point of zero charge of already less than approximately 7.2. In this case, it has been observed that the point of zero charge can be lowered, and that the immobilization of the PRP-T on the aluminium complexes is likewise reduced.

The term immobilization is understood to mean any form of linkage making the PRP-T inaccessible to dosage when, after centrifugation, the supernatant is collected.

The vaccine compositions according to the invention comprise the vaccine antigen formed by the PRP-T but can likewise comprise other vaccine antigens and especially those intended to protect against diphtheria, tetanus, whooping cough (cellular or acellular), poliomyelitis, hepatitis A, hepatitis B . . . etc. In fact, any vaccine antigen compatible with the PRP-T and the aluminium complexes is capable of entering into the vaccine composition according to the invention. It is thus possible to have liquid vaccine combinations allowing, in a single administration, vaccination against several illnesses. The vaccine compositions according to the invention are particularly adapted for administration to young children.

In addition, it has been observed that the use of such a liquid vaccine composition during the booster vaccination carried out in infants of 12 months who have received injections at 2, 4 and 6 months would allow the production of anti-PRP-T antibodies to be increased in a particularly increased manner with respect to a booster carried out under the same conditions with the TETRAct-HIB™ vaccine marketed by PASTEUR MERIEUX Sérums et Vaccins.

EXAMPLE 1

A vaccine composition is manufactured starting from the following constituents:

| | |
|---|---|
| Purified tetanus anatoxin (PTA) | 1 vaccinating unit |
| Purified diphtheria anatoxin (PDA) | 1 vaccinating unit |
| Pertussis cell mixture | 15 OU (opacimetric units) |
| PRP-T (expressed in weight of PRP) | 12 µg |
| Merthiolate | 43.75 µg |
| Aluminium hydroxide (expressed in Al) such as that present in the D.T. Coq | 0.3 mg |
| Phosphates | 30 µmol |
| 10 mmolar tris buffer comprising 8.5% sucrose | 0.125 ml |
| water for injection qsp | 0.5 ml |

The phosphate ions are added starting with a solution containing monopotassium phosphate, disodium phosphate and sodium chloride.

EXAMPLE 2

The immunogenicity of the vaccine composition obtained according to Example 1 was tested in young children in comparison to the immunogenicity of a vaccine of the previous type formed by the vaccine marketed under the name TETRAct-HIB™ and which has the same vaccine valencies but where the lyophilized retained PRP-T valency is reconstituted just before injection with the vaccine composition containing the diphtheria and tetanus anatoxins as well as the Pertussis cellular mixture.

This test was carried out on a group of 262 infants, of which 130 received the formulation according to Example 1 and 132 received the commercial vaccine TETRAct-HIB™. The administration of the vaccines was carried out at 2, 6 and 12 months intramuscularly.

Before immunization, the GMT titre of anti-PRP antibody was 0.2 µg/ml in the two groups; it was 1.9 and 1.4 µg after the second injection and 5.9 and 5.8 after the 3rd injection respectively for the vaccine according to the invention and the vaccine of the prior art.

After the second injection, 98% (with the vaccine according to the invention) and 93% (with the vaccine according to the prior art) of the infants had an anti-PRP antibody level of greater than 0.15 µg/ml; this level was attained after the 3rd injection in 100% of the infants receiving the vaccine according to the invention and in 99% of the infants receiving the vaccine according to the prior art.

After the 3rd injection, the quantities of antibodies directed against each of the vaccine valencies were on average the following:

| | Prior art vaccine | Invention vaccine |
|---|---|---|
| Diphtheria UI/ml | 1.35 | 1.56 |
| Tetanus UI/ml | 5.1 | 4.9 |
| Pertussis agglutin. titre GMT | 597 | 601 |
| PRP µg/ml | 5.8 | 5.9 |

After the booster injection carried out at 12 months, the quantities of antibodies this time were:

| | Prior art vaccine | Invention vaccine |
|---|---|---|
| Diphtheria UI/ml | 3.2 | 4.5 |
| Tetanus UI/ml | 12.0 | 11.5 |
| Pertussis agqlutin. titre GMT | 2447 | 2560 |
| PRP µg/ml | 19.4 | 32.6 |

These results show that the vaccine combination obtained according to the invention is stable; in fact the booster injection carried out on children 12 months old was carried out with a vaccine which had been manufactured 18 months previously; however, the results show that the immunogenicity of each of the antigens of the combination is retained. In addition, in a surprising manner, a booster effect which is clearly greater with the vaccine composition according to the invention is obtained, with respect to the booster effect obtained with a vaccine of the prior art having the same vaccine valencies.

EXAMPLE 3

Doses of vaccine composition such as described in Example 1 are kept at +4° C. for 18 to 24 months and then used in a clinical trial including 104 children.

The titres obtained for each of the vaccine valencies are summarized in the table below.

| | Before vaccinatian | After vaccination |
|---|---|---|
| Diphtheria G.M.T. | 0.013 | 0.736 |
| Tetanus G.M.T. | 0.181 | 3.831 |
| PRP G.M.T. µg/ml | 0.22 | 6.40 |

It can thus be seen that even after storage for a long period at +4° C., the vaccine composition according to the invention retains its immunogenic character, both as far as the PRP-T is concerned as well as the other vaccine antigens.

EXAMPLE 4

Vaccine compositions each comprising PRP-T at a concentration of 20 µg of PRP/ml are prepared in the presence of aluminium complexes of different types, and of different points of zero charge (PZC). The quantity of aluminium complexes is such that the concentration of aluminium in the composition is 0.6 g/l.

Composition 1: Aluminium complex formed by aluminium hydroxide such as that used in the D.T. Coq™ vaccine marketed by PMsv. PZC=11.3

Composition 2: Aluminium complex formed by aluminium hydroxide such as that used in the Recombivax® vaccine marketed by Merck. PZC=7.4

Composition 3: Aluminium complex formed by aluminium phosphate obtained by mixing sodium chloride and trisodium phosphate. PZC=6.2

Composition 4: Aluminium complex formed by the product called Alum and obtained by reaction of sodium carbonate in PBS buffer on potassium and aluminium sulphates. PZC=5.4

The vaccine compositions are obtained by simple mixture of the suspensions containing the aluminium complexes and PRP-T.

EXAMPLE 5

The immunogenicity of the different compositions obtained is tested in mice.

In order to verify the immunogenic stability, the compositions obtained are subjected to conditions of accelerated ageing, i.e. they are kept at 37° C. for 2 weeks.

The immunogenicity test is carried out on mice 22–24 g in weight to which doses of 0.5 ml each containing 2.5 µg of PRP are administered subcutaneously. The administrations are carried out on day 0 and on day 14. The blood of the mice is taken on day 14 and on day 21 and the level of antibodies is determined by radioimmunological determination. The number of mice inoculated for each vaccine composition is 8.

The result is considered satisfactory if:

there are at least 75% of the mice on day 21 which have a titre of ≧0.5, there is a significant difference between the results obtained on day 14 and those obtained on day 21.

It is considered that the vaccine composition obtained is stable if the results obtained after accelerated ageing are satisfactory.

The results obtained for the compositions tested are summarized in the table below:

|    | PZC  | Immuno. Test     |
|----|------|------------------|
| C1 | 11.3 | Not satisfactory |
| C2 | 7.4  | Not satisfactory |
| C3 | 6.2  | Satisfactory     |
| C4 | 5.4  | Satisfactory     |

It is thus seen that when the point of zero charge of the aluminium complexes is an acidic pH, the vaccine composition obtained is stable.

EXAMPLE 6

The percentage of PRP-T immobilized on the aluminium complexes is verified for each of the compositions of Example 4.

For this, each of the compositions is centrifuged; the supernatant is collected in which the quantity of non-immobilized PRP-T is measured by ELISA or by RIA.

The difference between the concentration of PRP-T in the starting composition and the quantity determined in the supernatant allows the percentage of immobilized PRP-T to be determined.

The results obtained are stated below:
C1: 100%
C2: 100%
C3: 100%
C4: 70%

EXAMPLE 7

Composition 1 is modified by adding phosphate ions to it in order to obtain a concentration of 50 mmol/l. The immunogenicity test carried out in mice after accelerated ageing of the solution then leads to a satisfactory result.

The determination of the percentage of immobilization of PRP-T on aluminium complexes shows that, under these conditions, only 20% of the PRP-T is immobilized.

EXAMPLE 8

Composition 1 is modified by this time adding citrate ions to it in order to obtain a concentration of 200 mmol/l.

The immunogenicity test carried out in mice after accelerated ageing of the solution then leads to a satisfactory result.

The determination of the percentage of immobilization of PRP-T on aluminium complexes shows that, under these conditions, the PRP-T is no longer immobilized at all.

EXAMPLE 9

Composition 2 is modified by adding phosphate ions to it in order to obtain a concentration of 20 mmol/l.

The immunogenicity test carried out in mice after accelerated ageing of the solution then leads to a satisfactory result. The determination of the percentage of immobilization of PRP-T on aluminium complexes shows that, under these conditions, the PRP-T is no longer immobilized at all.

EXAMPLE 10

Composition 3 is modified by adding phosphate ions to it in different quantities and the percentage of immobilization of PRP-T on the aluminium complexes is determined.

If the quantity of phosphate ions added is such that the concentration of phosphates in the composition is 2 mmol/l, the percentage of PRP-T immobilized is reduced to 10%.

If the quantity of phosphate ions added is such that the concentration of phosphates in the composition is 4 mmol/l, the PRP-T is no longer immobilized at all.

The immunogenicity tests carried out in mice after accelerated ageing of the solution are satisfactory.

EXAMPLE 11

Composition 4 is modified by adding phosphate ions to it to obtain a concentration of 60 mmol/l.

The determination of the percentage of PRP-T immobilized on the aluminium complexes shows that, under these conditions, only 30% of the PRP-T is immobilized. The immunogenicity test carried out in mice after accelerated ageing of the solution leads to a satisfactory result.

EXAMPLE 12

A vaccine composition is prepared starting from the following constituents:

| | |
|---|---|
| Aluminium hydroxide (expressed in Al) | 0.25 mg |
| PRP-T (expressed in weight of PRP) | 10 µg |

| -continued | |
|---|---|
| PDA | 1 vaccinating dose |
| PTA | 1 vaccinating dose |
| Phosphates | 15 μmoles |
| Polio antigens | |
| type I | 40 U |
| type II | 8 U |
| type III | 32 U |
| Pertussis anatoxin | 25 μg |
| Pertussis F-HA | 25 μg |
| 50 mmolar tris buffer comprising 42.5% sucrose | 0.125 ml |
| Water for injection qsp | 0.5 ml |

The immunogenicity tests relative to PRP-T carried out in mice with a solution prepared in this way as well as with a solution stored for 1 month at 37° C., a solution stored for 2 months at 25° C., and a solution stored for 6 months at 4° C., all led to satisfactory results, which shows the stability of PRP-T in such an environment.

EXAMPLE 13

A vaccine composition is prepared starting from the following constituents:

| | |
|---|---|
| Aluminium hydroxide (expressed in Al) | 0.3 mg |
| PRP-T (expressed in weight of PRP) | 10 μg |
| PDA | 1 vaccinating dose |
| PTA | 1 vaccinating dose |
| Pertussis anatoxin | 25 μg |
| F-HA | 25 μg |
| Hbs protein (such as presept in the GenHevac B PASTEUR ® vaccine) | 20 μg |
| Polio antigens | |
| type I | 40 U |
| type II | 8 U |
| type III | 32 U |
| Phosphates | 20 μmol |
| Carbonates | 5 μmol |
| 50 mmolar tris buffer comprising 42.5% sucrose | 0.125 ml |
| Water for injection qsp | 0.5 ml |

The stability of the solution prepared in this way is verified by submitting it to 2 weeks at 37° C. and by then carrying out an immunogenicity test of PRP-T in mice as described in Example 5.

The results obtained are satisfactory.

An immunogenicity test for the Hbs protein is carried out; this test is carried out in mice and consists in determining the anti-Hbs antibody by ELISA, then in determining the 50% effective dose which may, insofar as the test is considered satisfactory, be less than 0.970 μg of Hbs protein.

The results obtained with the solution prepared as indicated above and kept for 2 weeks at 37° C. before being tested were satisfactory.

EXAMPLE 14

A vaccine composition is prepared starting from the following constituents:

| | |
|---|---|
| Aluminium hydroxide (expressed in Al) | 0.3 mg |
| PRP-T (expressed in weight of PRP) | 10 μg |
| PDA | 1 vaccinating dose |
| PTA | 1 vaccinating dose |
| Pertussis anatoxin | 10 μg |
| F-HA | 5 μg |
| Fimbriae | 5 μg |
| Pertactin | 3 μg |
| Hbs protein (such as present in the GenHevac B PASTEUR®vaccine) | 20 μg |
| Polio antigens | |
| type I | 40 U |
| type II | 8 U |
| type III | 32 U |
| Phosphates | 20 μmol |
| Carbonates | 10 μmol |
| $MgCl_2$ | 5 μmol |
| 50 mmolar tris buffer comprising 42.5% sucrose | 0.125 ml |
| Water for injection gsp | 0.5 ml |

The immunogenicity tests relative to PRP-T carried out as described in Example 5, and those relative to the Hbs protein carried out as described in Example 13, all led to satisfactory results, showing the stability of the vaccine composition according to the invention.

What is claimed is:

1. A storage-stable, liquid vaccine composition comprising capsular polysaccharide of *Haemophilus influenzae* type b or polyribosylribitol phosphate having more than 100 monomer repeating units coupled to tetanus anatoxin as well as an aluminium-based adjuvant, wherein the aluminium-based adjuvant has a point of zero charge of less than approximately 7.2.

2. The vaccine composition according to claim 1, wherein the aluminium-based adjuvant comprises aluminium hydroxides to which anions have been added.

3. The vaccine composition according to claim 2, wherein the anions are chosen from amongst the phosphates and the citrates.

4. The vaccine composition according to claim 1, wherein the aluminium-based adjuvant comprises aluminium phosphates.

5. The vaccine composition according to claim 1, wherein the aluminium-based adjuvant comprises potassium and aluminium sulphates.

6. The vaccine composition according to claim 1, wherein said composition additionally comprises one or more of the vaccine valencies chosen from amongst: diphtheria, tetanus, whooping cough, hepatitis B and poliomyelitis.

7. A process for preparing a storage-stable, liquid vaccine composition comprising capsular polysaccharide of Haemophilus influenzae type b or polyribosylribitol phosphate having more than 100 monomer repeating units coupled to tetanus anatoxin, said process comprising obtaining a vaccine composition and adding an adjuvant to the vaccine composition by means of a suspension of aluminium complexes having a point of zero charge of less than approximately 7.2.

8. The process according to claim 7, wherein said adjuvant comprises aluminium hydroxides to which anions have been added.

9. The process according to claim 8, wherein said anions are chosen from amongst the phosphates and the citrates.

10. The process according to claim 7, wherein said aluminium-based adjuvant comprises phosphates.

11. The process according to claim 7, wherein said aluminium-based adjuvant comprises potassium and aluminium sulfates.

* * * * *